(12) United States Patent
Chen et al.

(10) Patent No.: US 11,721,083 B2
(45) Date of Patent: Aug. 8, 2023

(54) X-RAY IMAGING SYSTEM AND METHOD

(71) Applicant: Careray Digital Medical Technology Co., Ltd., Suzhou (CN)

(72) Inventors: Jian Chen, Suzhou (CN); Jianqiang Liu, Suzhou (CN)

(73) Assignee: CARERAY DIGITAL MEDICAL TECHNOLOGY CO., LTD., Suzhou (CN)

( * ) Notice: Subject to any disclaimer, the term of this patent is extended or adjusted under 35 U.S.C. 154(b) by 152 days.

(21) Appl. No.: 17/239,929

(22) Filed: Apr. 26, 2021

(65) Prior Publication Data
US 2021/0330275 A1 Oct. 28, 2021

Related U.S. Application Data

(60) Provisional application No. 63/016,575, filed on Apr. 28, 2020.

(30) Foreign Application Priority Data

May 8, 2020 (CN) .......................... 202010380071.4

(51) Int. Cl.
*A61B 6/00* (2006.01)
*G06K 9/78* (2006.01)
(Continued)

(52) U.S. Cl.
CPC ................ *G06V 10/22* (2022.01); *A61B 6/06* (2013.01); *A61B 6/4208* (2013.01);
(Continued)

(58) Field of Classification Search
CPC ......... A61B 6/544; A61B 6/469; A61B 6/588; A61B 6/589; A61B 6/542; A61B 6/06;
(Continued)

(56) References Cited

U.S. PATENT DOCUMENTS

| 5,539,798 A | 7/1996 | Asahina et al. |
| 2007/0025525 A1* | 2/2007 | Gilath .................... A61B 6/08 378/206 |

FOREIGN PATENT DOCUMENTS

| CN | 102961154 A | 3/2013 |
| CN | 203576524 U | 5/2014 |

(Continued)

OTHER PUBLICATIONS

International Search Report and Written Opinion issued in International Application No. PCT/CN2020/104337 dated Jan. 28, 2021, State Intellectual Property Office of the P.R. China, Beijing, China, 20 pgs.

*Primary Examiner* — Don K Wong
(74) *Attorney, Agent, or Firm* — Hauptman Ham, LLP

(57) ABSTRACT

Disclosed are an X-ray imaging system and method, and the system comprises an X-ray source, a high-voltage generator, a collimator, a digital flat-panel detector, and a host computer; a position relationship between a projection area and a subject is visually displayed through a display screen; as an image frame on the screen is directly dragged to a corresponding position of an image of the subject presented on the screen or an area of interest is drawn, the collimator automatically drives a collimating sheet to move and enables the projection area to move to an observation position required by the subject, and information about the area of interest is transmitted to the detector as an input for selecting a response area of automatic exposure control (AEC). The collimator cooperates with digital automatic exposure control (DAEC), so that a strict requirement is no longer existent for patient positioning.

10 Claims, 5 Drawing Sheets

(51) Int. Cl.
  *G06V 10/22* (2022.01)
  *G06T 7/70* (2017.01)
  *A61B 6/06* (2006.01)
  *G06V 10/10* (2022.01)
  *G06V 10/25* (2022.01)

(52) U.S. Cl.
  CPC ............ *A61B 6/4429* (2013.01); *A61B 6/463* (2013.01); *A61B 6/542* (2013.01); *G06T 7/70* (2017.01); *G06V 10/10* (2022.01); *G06V 10/25* (2022.01); *G06T 2207/30004* (2013.01); *G06V 2201/03* (2022.01)

(58) Field of Classification Search
  CPC ........... A61B 6/08; A61B 6/429; A61B 6/463; G06T 7/70; G06V 10/22; G06V 10/25; G06V 2201/03
  See application file for complete search history.

(56) References Cited

FOREIGN PATENT DOCUMENTS

| | | |
|---|---|---|
| CN | 106954329 A | 7/2017 |
| CN | 108095746 A | 6/2018 |
| CN | 110960243 A | 4/2020 |

\* cited by examiner

ND METHOD

CROSS REFERENCE TO RELATED APPLICATION

This application claims the benefit of priority to U.S. Provisional Patent Application No. 63/016,575, filed Apr. 28, 2020, entitled AN INTELLIGENT X-RAY IMAGING SYSTEM, and the benefit of priority to Chinese Patent Application No. 2020103800714, filed May 8, 2020, entitled X-RAY IMAGING SYSTEM AND METHOD, which are hereby incorporated by reference herein in its entirety.

FIELD OF TECHNOLOGY

The present disclosure generally relates to an X-ray detector imaging field, and more particularly relates to an X-ray imaging system and method.

BACKGROUND

At present, key components of X-ray imaging equipment have little cooperation with each other, and application potential of the components beyond its basic functions has not been exploited. For example: 1. A collimator is just a simple X-ray range adjustment device; 2. Disadvantages, for example, the automatic exposure control area is limited, and additional devices (ionization chamber) and cost are required, and dose is wasted as the devices absorb X-rays, and patient positioning requires precise positioning.

SUMMARY

An aspect relates to an X-ray imaging system and method, which can improve the coordinated action of a collimator and a detector, and can automatically and intelligently complete the X-ray inspection of a subject with a simple operation, wherein technical solutions are as follows:

In one aspect, the present disclosure provides an X-ray imaging system, comprising an X-ray source, a high-voltage generator, a collimator, a digital flat-panel detector, and a host computer, wherein the host computer is configured to implement a signal transmission and processing among the X-ray source, the high-voltage generator, the collimator and the digital flat-panel detector, wherein the collimator comprises collimating sheet assembly that makes light form a projection area on a subject, the digital flat-panel detector is configured to have a DAEC (digital automatic exposure control) function and can generate DAEC parameters, and the parameters comprise an actual DAEC response area and a target gray value;

The system further comprises a PLC and a camera for capturing an image of the subject to present a position and/or contour of the subject;

The PLC is configured to display the image captured by the camera on a display screen, and generate a coordinate system and a projection image frame corresponding to the X-ray projection area on the display screen, wherein the pixels of the captured image and the coordinate points of the coordinate system form a one-to-one correspondence, and the PLC is configured to automatically determine the projection area and the actual DAEC response area to desired positions according to a demand of the captured image and a diagnostic part and/or position;

The projection area is configured to be adjusted according to the demand of the diagnostic part and/or position or an adjustment of the projection image frame, and the projection area is adjusted by the collimating sheet assembly; the actual DAEC response area is configured to be adjusted according to the adjustment of the demand of the diagnostic part and/or position, and the actual DAEC response area is adjusted by the digital flat-panel detector; the projection area is configured to cover the actual DAEC response area, the display screen is a display screen connected to the PLC; the PLC is arranged in the collimator; the projection image frame and a frame of the response area would or would not be displayed on the display screen.

In one aspect, the present disclosure provides an X-ray imaging system, comprising an X-ray source, a high-voltage generator, a collimator, a digital flat-panel detector, and a host computer, wherein the host computer is configured to implement a signal transmission and processing among the X-ray source, the high-voltage generator, the collimator and the digital flat-panel detector, wherein the collimator comprises a collimating sheet assembly that makes light form a projection area on a subject, the digital flat-panel detector has a DAEC function and can generate DAEC parameters, and the parameters comprise an actual DAEC response area and a target gray value;

The system further comprises a camera for capturing an image of the subject to present a position and/or contour of the subject, and an adjustment module for automatically adjusting the projection area and the actual DAEC response area to a desired position according to the image captured by the camera and a demand of a diagnostic part and/or position.

Further, the projection area is configured to cover the actual DAEC response area.

Further, the adjustment module comprises a PLC, the PLC is configured to display the image captured by the camera on a display screen, and generate a coordinate system and a projection image frame corresponding to the projection area on the display screen, wherein pixels of the captured image and coordinate points of the coordinate system form a one-to-one correspondence;

As the projection image frame corresponding to the projection area is generated on the display screen, the projection area is configured to be adjusted according to the adjustment of the demand of the diagnostic part and/or position or an adjustment of the projection image frame, and the actual DAEC response area is configured to be adjusted according to the demand of the adjustment of the diagnostic part and/or position.

Further, the display screen is a display screen connected to the PLC or a display screen connected to a host computer.

Further, the PLC is a part of the host computer or is arranged in the collimator, and the projection image frame and a frame of the response area would or would not be displayed on the display screen.

Further, the adjustment module comprises an intelligent recognition module for recognizing an examined part of the subject presented by the camera, wherein the intelligent recognition module is connected with the collimator;

the intelligent recognition module is configured to adjust the projection area and the actual DAEC response area according to a demand of an input diagnostic part and/or position as the intelligent recognition module has recognized the examined part of the subject, a positional relationship between the examined part and a current projection area, and a positional relation between the examined part and a current actual DAEC response area.

In another aspect, the present disclosure also provides an imaging method based on the above system, wherein a maximum exposure acceptance range of a detector is configured to be an effective imaging area, wherein the method comprises the following steps:

a1. causing a subject to be X-ray imaged to enter the imaging system to ensure that the subject is within the effective imaging area;

b1. photographing the subject by the camera, displaying an image captured by the camera on a display screen, and generating a coordinate system and a projection image frame corresponding to a projection area on the display screen by an adjustment module;

c1. adjusting the projection area and an actual DAEC response area to a desired position by the adjustment module according to a demand of a diagnostic part and/or position;

d1. determining a target gray value according to the demand of the diagnostic part and/or position;

e1. automatically informing a high-voltage generator to stop exposure according to a DAEC parameter during the X-ray photographing process, and obtaining an X-ray image by the detector;

wherein step c1 and step d1 are in no particular order.

In another aspect, the present disclosure also provides an imaging method based on the above system, wherein a maximum exposure acceptance range of a digital flat-panel detector is configured to be an effective imaging area, wherein the method comprises the following steps:

a2. causing a subject to be X-ray imaged to enter the imaging system to ensure that the subject is within the effective imaging area;

b2. photographing the subject by the camera, displaying an image captured by the camera on a display screen, and generating a coordinate system and a projection image frame corresponding to a projection area on the display screen by an adjustment module;

c2. touching the projection image frame on the display screen and dragging it to a desired observation position; or circling or pointing out an area of interest on the display screen to form a new image frame, a PLC is configured to convert a displacement of each side of the image frame on the display screen into the respectively required adjustment displacement of a collimating sheet assembly; a projection area is configured to be formed as the collimating sheet assembly is respectively adjusted to a required coverage position;

d2. transmitting a position information of the area of interest to the flat-panel detector, and adjusting DAEC parameter according to the position information of the area and a demand of a diagnostic part and/or position by the flat-panel detector;

e2. starting to expose as an action of the collimating sheet assembly is completed and the DAEC parameter is determined;

f2. automatically informing a high-voltage generator to stop exposure according to the automatic exposure control parameter, and obtaining an X-ray image by the detector.

In another aspect, the present disclosure also provides an imaging method based on the above system, the system further comprising an intelligent recognition module for recognizing an examined part of a subject presented on a display screen by a camera, and a maximum exposure acceptance range of a digital flat-panel detector is configured to be an effective imaging area, wherein the digital flat-panel detector has a function for automatically generating a DAEC parameter, wherein the method comprises the following steps:

a3. causing a subject to be X-ray imaged to enter the imaging system to ensure that the subject is within the effective imaging area;

b3. photographing the subject and the detector by the camera, and recognizing the examined part of the subject, a positional relationship between the examined part and a current projection area, and a positional relation between the examined part and a current actual DAEC response area by the intelligent recognition module after receiving and processing a captured image;

c3. adjusting the projection area and the actual DAEC response area by the intelligent recognition module according to a demand of a diagnostic part and/or position;

d3. adjusting an automatic exposure control parameter through the flat-panel detector according to the demand of the diagnostic part and/or position;

e3. starting to expose as an action of a collimating sheet assembly is completed and the automatic exposure control parameter is determined;

f3. automatically informing a high-voltage generator to stop exposure according to the automatic exposure control parameter, and obtaining an X-ray image by the detector.

The beneficial effects brought by the technical solution provided in the present disclosure are as follows: The position relationship between the projection area and the subject can be displayed intuitively on the display screen, and the image frame on the display screen can be directly dragged to the corresponding position of the image of the subject on the display screen or the area of interest can be drawn, and the collimating sheet assembly automatically drives the collimating sheet to move and drives the projection area to the observation position required by the subject; at the same time, the information of the area of interest is transmitted to the detector as the input of the response area selecting the automatic exposure control (DAEC), and the collimator and DAEC cooperates with each other and no longer has strict requirements on patient positioning.

BRIEF DESCRIPTION

Some of the embodiments will be described in detail, with references to the following Figures, wherein like designations denote like members, wherein.

DETAILED DESCRIPTION

Figure 1:
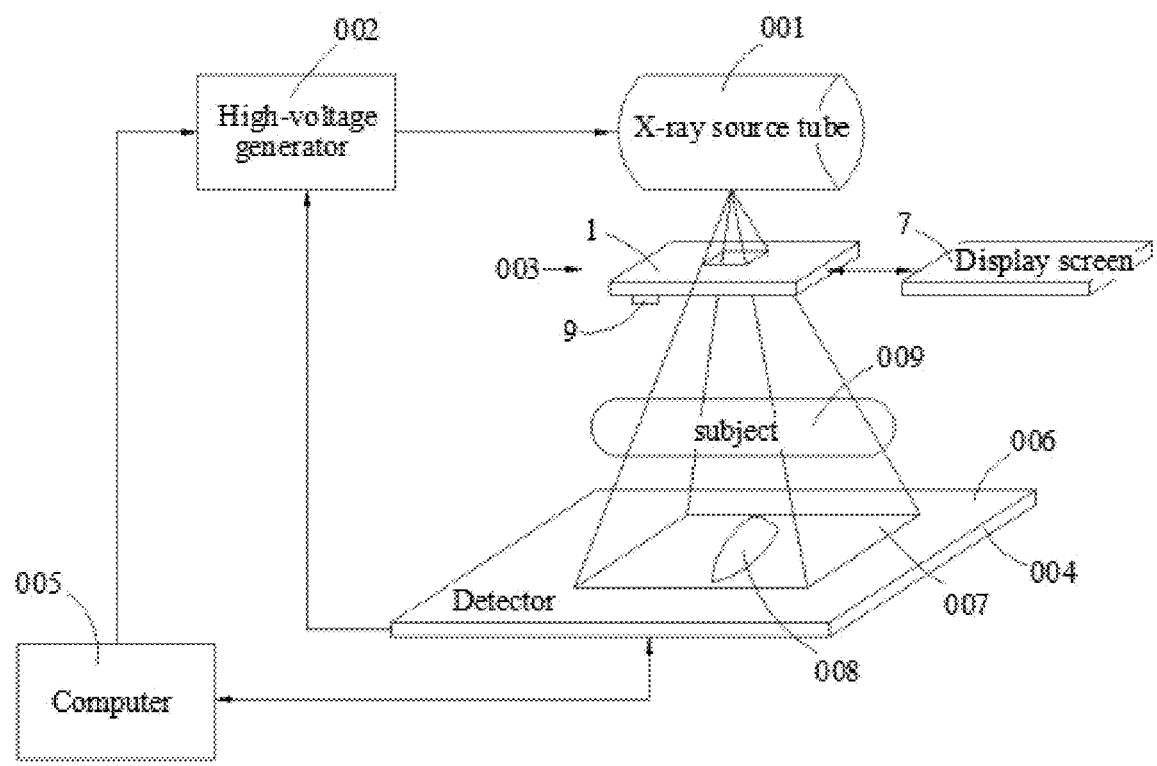
FIG. 1 is a schematic structure diagram of X-ray imaging system provided by an embodiment of the present disclosure.
Figure 2:
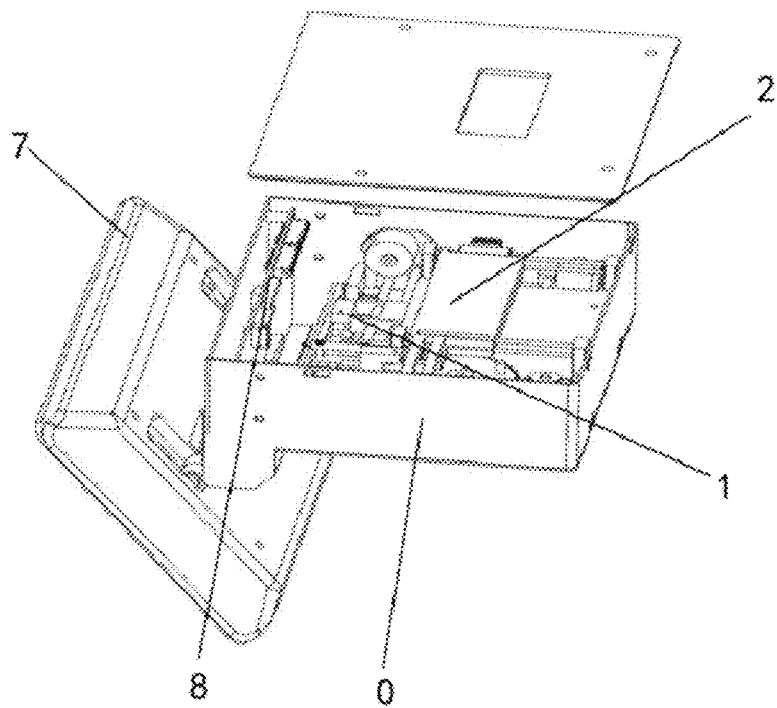
FIG. 2 is a schematic structure diagram of a collimator provided by an embodiment of the present disclosure.

In order to enable those skilled in the art to better understand the solutions of the present disclosure, the technical solutions in the embodiments of the present disclosure are explained clearly and completely below in conjunction with the accompanying drawings, and apparently, the described embodiments are merely a part of the embodiments of the present disclosure, not all the embodiments. Based on the embodiments of the present disclosure, all other embodiments Obtained by one of ordinary skill in the art without creative work fall within the protective scope of the present disclosure.

It should be noted that terms "first", "second" and the like in the description, the claims and the accompanying drawings of the present disclosure are used to distinguish similar objects, and do not have to be used to describe a specific order or sequence. It should be understood that the data so used can be interchanged under appropriate circumstances so that the embodiments of the present disclosure described herein can be implemented in an order other than those illustrated or described herein. In addition, the terms "comprise" and "have" and any variations thereof are intended to cover non-exclusive inclusions, for example, processes, methods, devices, products or equipment that include a series of steps or units are not necessarily limited to those clearly listed steps or units, but may include other steps or units not explicitly listed or inherent to these processes, methods, products or equipment.

In an embodiment of the present disclosure, an X-ray imaging system is provided, the system comprises an X-ray source 001, a high-voltage generator 002, a collimator 003, a digital flat-panel detector 004, and a host computer 005, wherein the host computer 005 is configured to implement a signal transmission and processing among the X-ray source 001, the high-voltage generator 002, the collimator 003 and the digital flat-panel detector 004; the collimator 003 comprises a collimating sheet assembly that makes light form a projection area on a subject, the digital flat-panel detector 004 has a DAEC function and can generate DAEC parameters, and the parameters comprise an actual DAEC response area 008 and a target gray value; the projection area 007 covers the actual DAEC response area 008; the system further comprises a camera 9 for capturing an image of the subject to present a position and/or contour of the subject, and an adjustment module for automatically adjusting the projection area and the actual DAEC response area 008 to desired positions according to the image captured by the camera 9 and the demand of an diagnostic part and/or position.

The adjustment module comprises a PLC (programmable logic controller) 8, and the PLC 8 is configured to display the image captured by the camera 9 on a display screen 7, and generate a coordinate system and a projection image frame corresponding to the projection area 007 on the display screen 7, wherein the pixels of the captured image and the coordinate points of the coordinate system form a one-to-one correspondence, and the PLC 8 is used to automatically determine the projection area and the actual DAEC response area to desired positions according to the captured image and the demand of the diagnostic part and/or position;

as the projection image frame corresponding to the projection area 007 and a response area image frame corresponding to the actual DAEC response area 008 are generated on the display screen 7, the projection area 007 is adjusted according to the adjustment of the demand of the diagnostic part and/or position or the adjustment of the projection image frame, wherein the adjustment action thereof is carried out by the collimating sheet assembly, and the actual DAEC response area 008 is adjusted according to the demand of the diagnostic part and/or position or the adjustment of the projection image frame, wherein the adjustment action thereof is carried out by the digital flat panel detector 004.

The display screen 7 is a display screen connected to the PLC 8 or a display screen connected to a host computer 005; the PLC 8 is a part of the host computer 005 or is arranged in the collimator 003; and the projection image frame and a frame of the response area would or would not be displayed on the display screen.

Embodiment 1

As shown in FIGS. 1-6, an X-ray imaging system comprises an X-ray source 001, a high-voltage generator 002, a collimator 003, a digital flat-panel detector 004, and a host computer 005.

The digital flat-panel detector has a DAEC function and can generate DAEC parameters, which is disclosed in the patent with patent publication No. CN106954329B. An exposure system disclosed in the patent automatically generates DAEC parameters, which comprise an actual DAEC response area 008 and a target gray value.

The host computer 005 implements the signal transmission and processing among the X-ray source 001, the high-voltage generator 002, the collimator 003 and the digital flat-panel detector 004, and the collimator comprises a housing 0, a camera 9 mounted to the housing 0, a PLC 8, a filter assembly 2, a collimating sheet assembly 1, a display screen 7 and an X-ray detector. In this embodiment, the display screen 7 is connected with the PLC 8; the PLC 8 is arranged in the housing 0; the camera 9 comprises one RGB camera, and the PLC 8 displays the image of the subject 009 captured by the camera 9 on the display screen 7; the collimating sheet assembly 1 causes the light to form a projection area 007 on the subject 009, and the PLC 8 generates a coordinate system on the display screen 7, and corresponds the image captured by the camera 9 to the coordinate system of the display screen 7. An image frame corresponding to the projection area 007 can be generated on the display screen. An adjustment module comprises the camera 9, the PLC 8 and the display screen 7, and the display screen 7 is a touch screen, which can intuitively display the positional relationship between the projection area and the subject.

The filter assembly 2 comprises a first mounting plate 21, a first upper slide bar 22 and a first lower slide bar 23 mounted on the first mounting plate 21, and a first filter 24 and a second filter 25 slidably connected to the first upper slide bar 22 and the first lower slide bar 23; on the same side of the first filter 24 and the second filter 25 are provided with guide grooves 26. There are two first upper slide bars 22 and two first lower slide bars 23 respectively arranged in parallel, and the first upper slide bars 22 are located above the first lower slide bars 23; the filter assembly 2 further comprises a first drive motor 27 mounted on the first mounting plate 21, a first variable gear 28 fixedly sleeved on a rotating shaft of the first drive motor 27, a second gear 29 rotatably connected to the first mounting plate 21 and in transmission connection with the first variable gear 28, a first guide rod 20 and a second guide rod 210 fixed on the end surface of the second gear 29, a first travel sensor 211 for detecting a movement position of the filters by counting the number of turns of the second gear 29, and an illuminometer assembly 212, wherein the first guide rod 20 is inserted in the guide grooves 26 on the first filter 24, and the second guide rod 210 is inserted in the guide grooves 26 on the second filter 25, and the second gear 29 is configured to rotate to drive the first filter 24 and the second filter 25 to slide in opposite directions respectively on the first upper slide bars 22 and the first lower slide bars 23.

The collimating sheet assembly 1 comprises a second mounting plate 11, an upper support 12 and a lower support 13 mounted on the second mounting plate 11, an upper guide shaft 14 and a lower guide shaft 15 respectively mounted on the upper support 12 and the lower support 13, an upper shielding sheet 16 and a lower shielding sheet 17 slidably connected to the upper guide shaft 14 and the lower guide shaft 15, an upper driving screw mechanism_ and a lower driving screw mechanism for respectively driving the upper shielding sheet 16 to slide on the upper guide shaft 14 and driving the lower shielding sheet 17 to slide on the lower guide shaft 15, and an upper travel sensor 18 and a lower travel sensor 19 for respectively detecting a moving distance of the upper shielding sheet 16 and a moving distance of the lower shielding sheet 17, wherein the sliding directions of the upper shielding sheet 16 and the lower shielding sheet 17 are perpendicular to each other. The upper driving screw mechanism comprises an upper second motor 10, an upper second gear set 111 in transmission connection with the upper second motor 10, an upper screw 112 arranged in parallel with the upper guide shaft 14, and an upper mounting frame 113 fixedly connected with a transmission nut of the upper screw 112, wherein the upper screw 112 is in transmission connection with the upper second gear set 111, and the upper shielding sheet 16 is mounted on the upper mounting frame 113, and there are respectively two upper mounting frames 113 and two upper shielding sheets 16. The lower driving screw mechanism comprises a lower second motor 110, a lower second gear set 114 in transmission connection with the lower second motor 110, a lower screw 115 arranged in parallel with the lower guide shaft 15, and a lower mounting frame 116 fixedly connected with a transmission nut of the lower screw 115, wherein the lower screw 115 is in transmission connection with the lower second gear set 114, and the lower shielding sheet 17 is mounted on the lower mounting frame 116, and there are respectively two lower mounting frames 116 and two lower shielding sheets 17.

Figure 3:
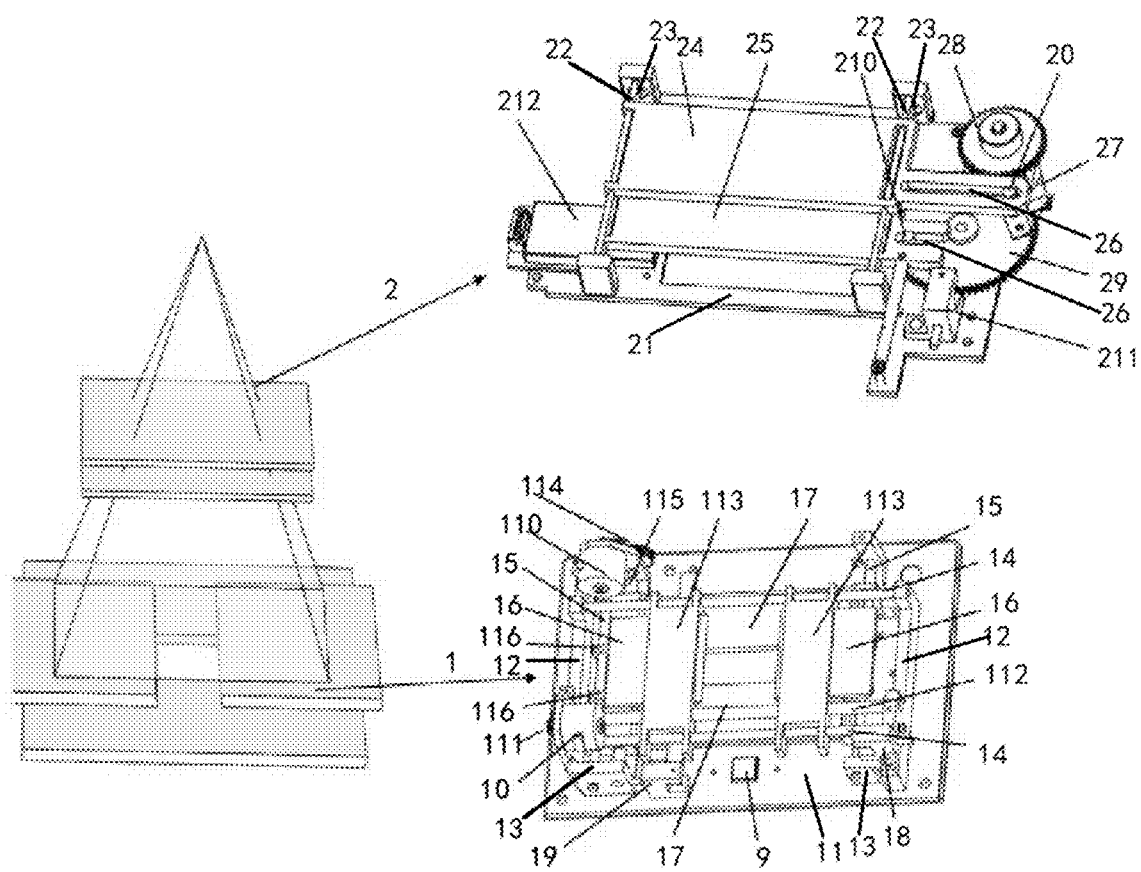
FIG. 3 is a schematic structure diagram of a filter assembly and a collimating sheet assembly provided by an embodiment of the present disclosure.
Figure 4:
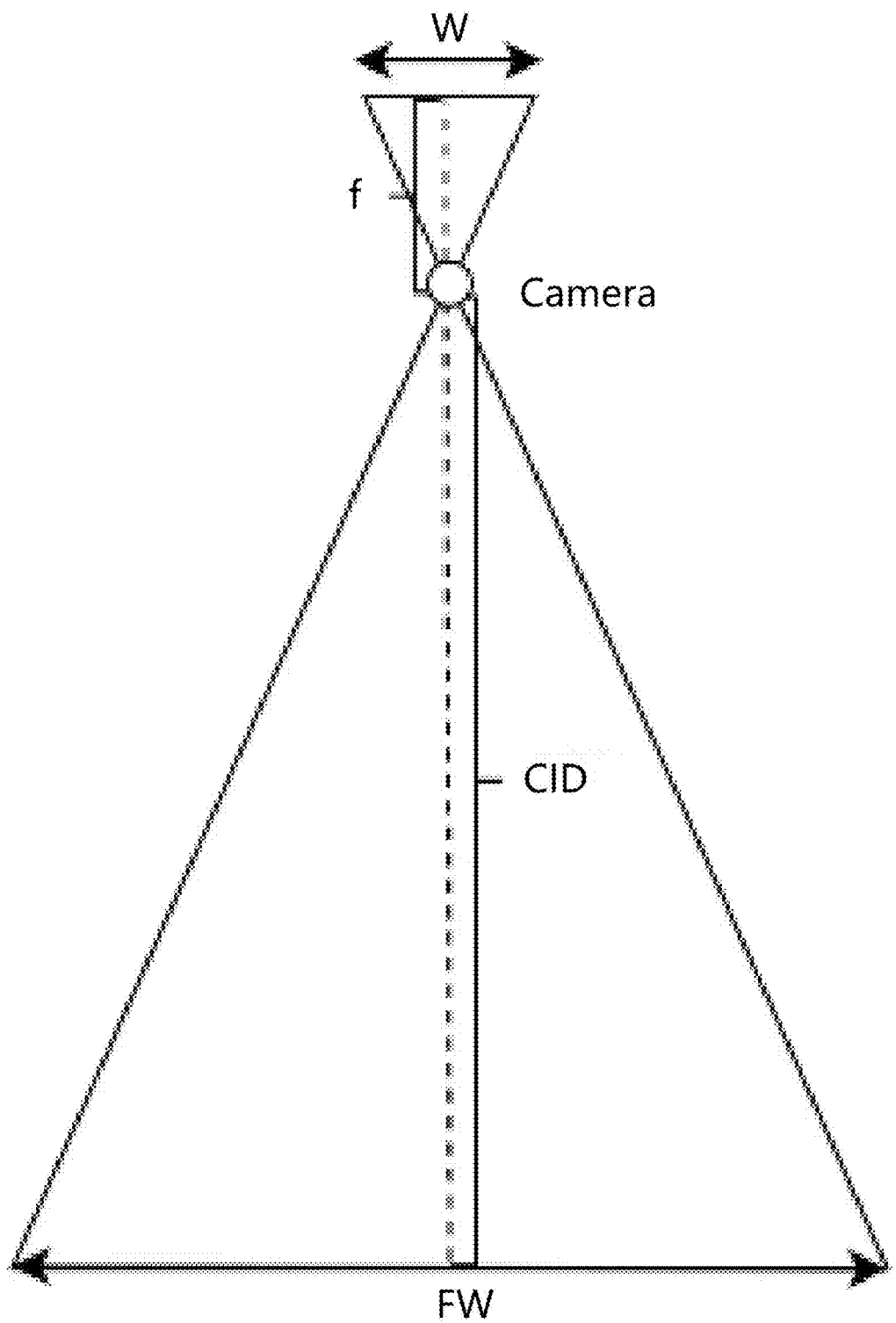
FIG. 4 is a schematic diagram of a pinhole model provided by an embodiment of the present disclosure.
Figure 5:
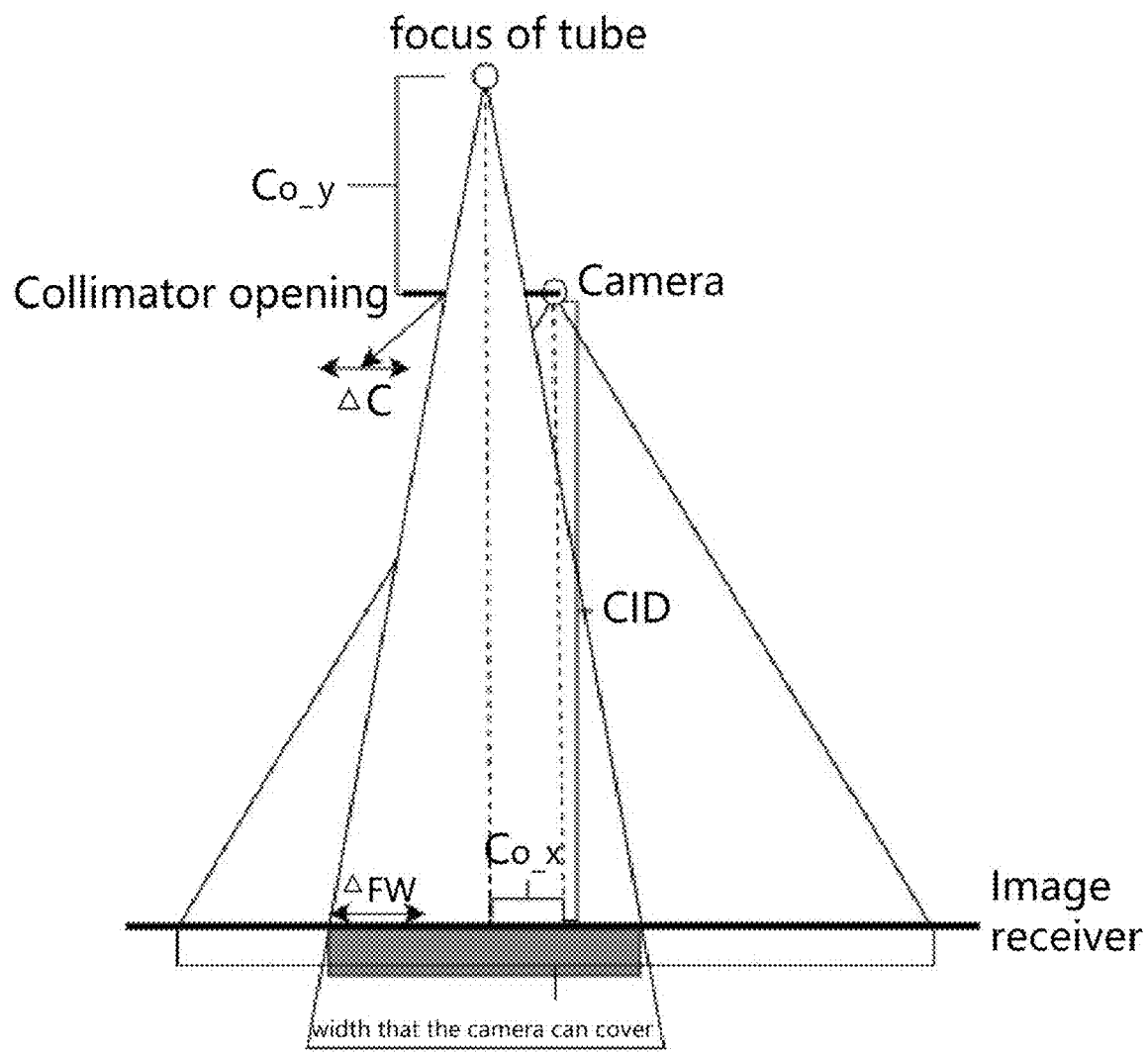
FIG. 5 is the corresponding relationship among adjustment of screen pixels, displacement of a receiver and displacement of a collimating opening provided by an embodiment of the present disclosure.
Figure 5:
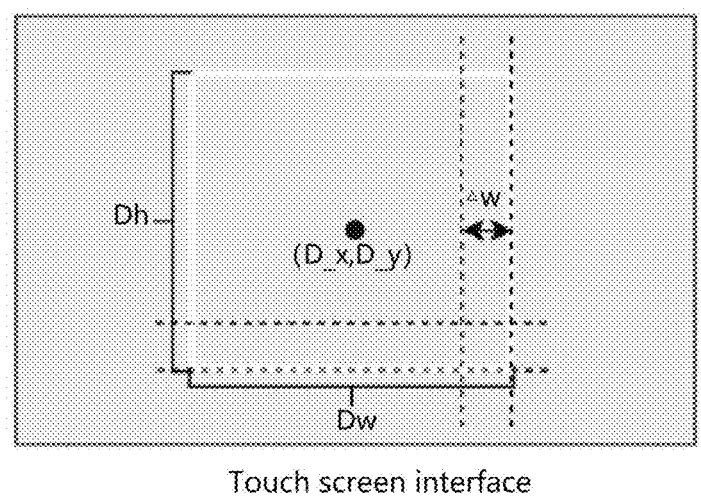
Figure 6:
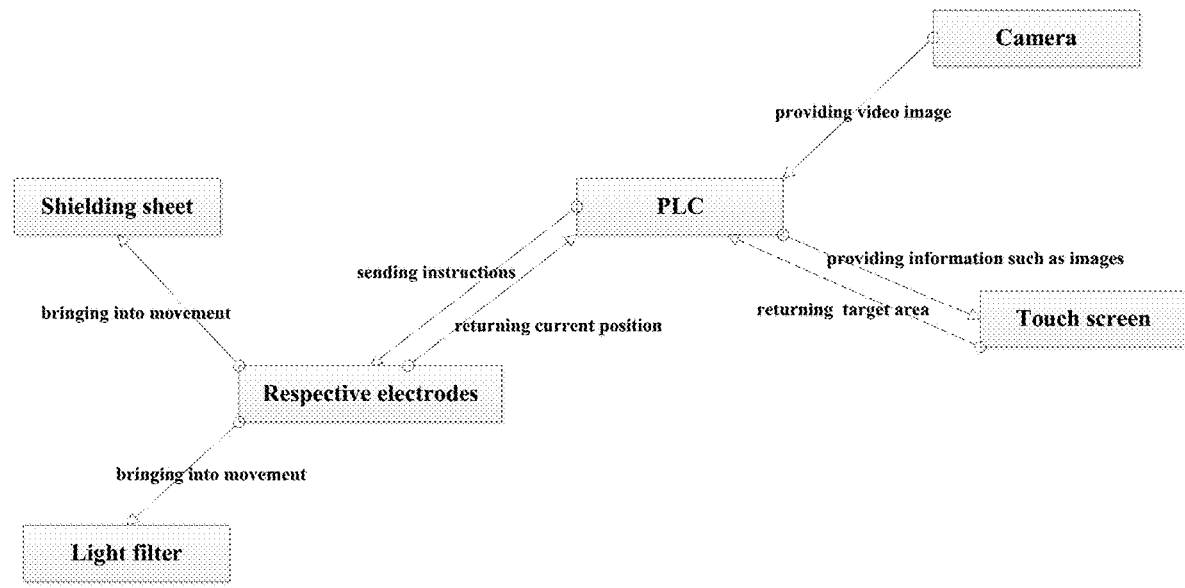
FIG. 6 is a schematic diagram of the working flow of the collimator provided by an embodiment of the present disclosure.

The principle of imaging and projection area 007 will be described in detail with reference to FIG. 4:

1. The relevant variables and constants are as follows:
   Co_y(collimator_offset_y): an offset distance from a collimator opening to a focus of X-ray tube in vertical direction (unit: mm)
   Co_x(camera_offset_x): an offset distance between a camera and a focus of tube in horizontal direction (unit: mm)
   Dw(detector_width): a width of an imaging area of an X-ray detector unit: mm)
   Dh(detector_height): a height of an imaging area of an X-ray detector (unit: mm)
   D_x, D_y): a center coordinate of the Cray detector displayed in a screen unit: pixel)
   CID(camera to image-receptor distance): a distance from a camera to an image-receiver (unit:
   FW(field_wdth): a width that a camera can cover when the Cliff determined (unit: mm)
   w(widthpixel): a width of an image in pixels (unit: pixel)
   f: a intrinsic parameter of a camera
2. the intrinsic parameter of a camera
As shown in FIG. 3, the width of an image in pixels is correspondingly obtained according to a pinhole model:

$$w = f\frac{FW}{CID}$$

wherein, the camera parameter f is provided by the camera manufacturer.

3. Correspondence among adjustment of screen pixels, a displacement of a receiver, and a displacement of a collimating opening 1) An interactive interface adjusts the pixels by Δw (pixel), and the imaging area of an X-ray detector is shifted by ΔFW (mm). From the previous formula:

$$FW = \frac{CID}{f} * w$$

A discretization form could be available:

$$\Delta FW = \frac{CID}{f} * \Delta w$$

in the formula, CID is a distance from the camera to the imaging area of the X-ray detector, which can be measured in real time; f is a known value; as the width of the interactive interface is shifted by Δw (pixel), the imaging area of the X-ray detector is shifted by ΔFW(mm).

2) The interactive interface adjusts the pixels by Δw (pixel), and the collimator opening driving motor is shifted by Δc (mm). From the similar triangle formulas:

$$\frac{\Delta c}{\Delta FW} = \frac{Co\_y}{CID + Co\_y}$$

Following formula could be derived:

$$\Delta c = \frac{Co\_y}{CID + Co\_y}\Delta FW$$

The ΔFW is brought in to obtain the following formula:

$$\Delta c = \frac{CID}{f} * \frac{Co\_y}{CID + Co\_y}\Delta w$$

in the formula, CID is the distance from the camera to the imaging area of the X-ray detector, which can be measured in real time, the rest parameters are known values; as the width of the interactive interface is shifted by Δw (pixel), the collimator opening is shifted by Δc (mm).

Correspondingly, the number of pulses that the system needs to send to the stepper motor driver can be obtained. As a single pulse displacement of the stepper motor is known as:

$$\frac{n\theta}{360°} * k * L,$$

where θ is a step angle, n is a subdivision number of the driver, k is a gear ratio, and L is a lead of screw. Therefore, when is required to shift the collimator opening by Δc, the number of pulses N_pulse that the system needs to send to the driver is:

$$N\_pulse = \frac{\Delta c}{\frac{n\theta}{360°} * k * L}$$

The adjustment of parameter of the detector refers to the exposure system disclosed in the patent with patent publication number CN106954329B, which is hereby incorporated by reference herein in its entirety.

As shown in FIG. 1, the maximum exposure acceptance range of the detector is the effective imaging area 006, and an imaging method based on the above system, comprises the following steps:

a. A subject 009 to be X-ray imaged is configured to enter the imaging system to ensure that the subject 009 is within the effective imaging area 006;

b. The camera 9 is configured to display the subject 009 and the projection area 007 on the display screen 7 in real-time;

c. The projection area 007 has a corresponding projection image frame on the display screen 7, and the user touches the projection image frame on the display screen 7 and drags it to a desired observation position; the PLC 8 converts the displacement of each side of the projection image frame on the display screen 7 into the respectively required adjustment displacement of the collimating sheet assembly 1, and then each side of the projection image frame is respectively adjusted to the required coverage position by the collimating sheet assembly, to form the projection area 007;

d. The desired filter serial number is selected on the display screen 7, and the action of the filter assembly 2 is controlled by the PLC to be adjusted to a desired filter;

e. The position information of the area of interest is transmitted to the flat-panel detector 004, and the flat-panel detector 004 calculates the automatic exposure control parameters (DAEC parameters) according to the information of the area and the demand of the diagnostic part and/or position;

f. The system starts to expose after the actions of the collimating sheet assembly 1 and the filter assembly 2 have been completed;

g. According to the automatic exposure control parameters, the detector automatically informs the high-voltage generator to stop exposure, and an X-ray image is Obtained.

Through the above-mentioned device and method, the simple signal transmission between independent components is converted into the coordinated action between the components, the application potential in addition to the basic functions among the components is opened up, for example: the original collimator is just a simple X-ray range adjustment equipment, but through the above-mentioned system, it can also provide information such as patient status for imaging.

The automatic exposure control area is no longer limited, and no additional device (ionization chamber) is needed, which reduces equipment cost, reduces the dose waste caused by the absorption of X-rays by the device, and the patient positioning no longer requires a precise position.

Embodiment 2

The difference between this embodiment and Embodiment 1 is that each collimating sheet in collimating sheet assembly 1 is controlled by a screw assembly, so that the projection area 007 and the actual DAEC response area 008 are determined by circling the area of interest, the PLC 8 only needs to control respective screw assemblies to realize the independent action of each collimating sheet and make the projection area cover the circled observation area, and the conversion principle of the area change sensed by the display screen and the action of each screw assembly to realize the displacement of the collimating sheet is the same as that of Embodiment 1.

The maximum exposure acceptance range of the detector is the effective imaging area 006, and an imaging method based on the above system, comprises the following steps:

a. A subject 009 to be X-ray imaged is configured to enter the imaging system to ensure that the subject 009 is within the effective imaging area 006;

b. The camera 9 is configured to display the subject 009 and the projection area 007 on the display screen 7 in real-time;

c. The area of interest on the display screen 7 is circled or pointed out by user to form an image frame, and the PLC 8 converts the displacement of each side of the image frame on the display screen 7 into the respectively required adjustment displacement of the collimating sheet assembly 1, and then each side of the image frame is respectively adjusted to the required coverage position by the collimating sheet assembly 1, to form the projection area 007;

d. The desired filter serial number is selected on the display screen 7, and the action of the filter assembly 2 is controlled by the PLC controlled to be adjusted to the desired filter;

e. The information of the area of interest is transmitted to the flat-panel detector 004, and the flat-panel detector 004 calculates the automatic exposure control parameters according to the information of the area and the demand of the diagnostic part and/or position;

e. The system starts to expose after the actions of the collimating sheet assembly 1 and the filter assembly 2 have been completed;

f. According to the automatic exposure control parameters, the detector automatically informs the high-voltage generator to stop exposure, and an X-ray image is obtained.

Embodiment 3

Figure 7:
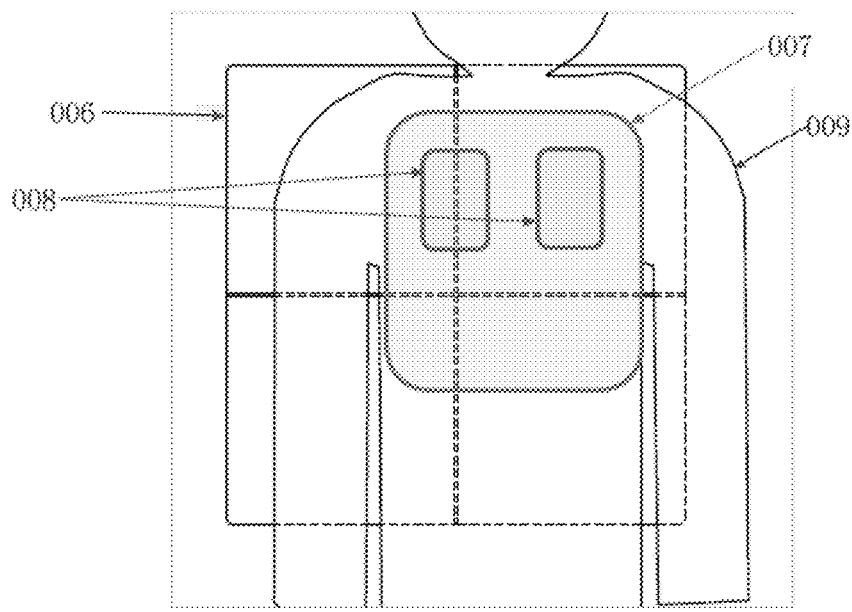
FIG. 7 is a schematic diagram of a positional relationship of each area during exposure provided by an embodiment of the present disclosure.

As shown in FIG. 7, the difference between this embodiment and Embodiment 1 is that the adjustment module is an intelligent recognition module for recognizing the examined part of the subject presented by the camera, the intelligent recognition module is connected with the collimator and the digital flat-panel detector, and after the intelligent recognition module recognizes the examined part of the subject, the positional relationship between the examined part and a current projection area, and the positional relation between the examined part and a current actual DAEC response area, the intelligent recognition module adjusts the projection area and the actual DAEC response area according to the demand of the input diagnostic part and/or position.

The maximum exposure acceptance range of the detector is the effective imaging area 006, and an imaging method based on the above system, in which the digital flat-panel detector has a DAEC function and can generate DAEC parameters, the intelligent recognition module stores DAEC parameter configurations for various parts of the subject, and when the intelligent recognition module recognizes the part of the subject to be imaged, it will automatically output DAEC parameters matching the part;

The method comprises the following steps:

a. causing a subject to be X-ray imaged to enter c imaging system to ensure that the subject is within the effective imaging area;

b. photographing the subject and the detector by the camera, transferring the photographed image to the intelligent recognition module, and recognizing the examined part of the subject, the positional relationship between the examined part and the current projection area, and the positional relation between the examined part and the current actual DAEC response area by the intelligent recognition module;

c. adjusting the projection area and the actual DAEC response area through the intelligent recognition module according to the demand of the input diagnostic part and/or position;

d. adjusting the automatic exposure control parameters through the flat-panel detector according to the demand of the diagnostic part and/or position;

e. starting to expose after completing the action of the collimating sheet assembly and the filter assembly and determining the automatic exposure control parameters;

f. automatically informing the high-voltage generator to stop exposure by a detector according to the automatic exposure control parameters, and obtaining an X-ray image.

In Step c, the position of the actual DAEC response area is determined when the demand of the diagnostic part and/or position is determined, for example, if the examined part is a lung, and after the projection area is determined, the detector will automatically determine the position and shape of the required actual DAEC response area according to the requirement that the examined part is the lung, and automatically carry out adjustment while determining the target gray value, and then perform exposure, same as Embodiments 1 and 2.

Embodiment 4

As shown in FIGS. 1-6, an X-ray imaging system comprises an X-ray source 001, a high-voltage generator 002, a collimator 003, a digital flat-panel detector 004, and a host computer 005, wherein the host computer 005 comprises a. PLC 8 and a display screen 7.

The digital flat-panel detector has a DAEC function and can generate DAEC parameters, which is disclosed in the patent with patent publication No. CN106954329B. An exposure system disclosed in the patent automatically generates DAEC parameters, and the DAEC parameters comprise an actual DAEC response area 008 and a target gray value.

The host computer 005 implements the signal transmission and processing among the X-ray source 001, the high-voltage generator 002, the collimator 003 and the digital flat-panel detector 004, and the collimator comprises a housing 0, a camera 9 mounted to the housing 0, a filter assembly 2, a collimating sheet assembly 1, a display screen 7 and an X-ray detector in this embodiment, the display screen 7 is connected with the PLC 8, the camera 9 comprises an RGB camera, which proportionally displays the subject 009 on the display screen 7 through the PLC 8; the collimating sheet assembly 1 causes the light to form a projection area 007 on the subject 009, and the PLC 8 generates a coordinate system on the display screen 7, and corresponds the image captured by the camera 9 to the coordinate system of the display screen 7. An image frame corresponding to the projection area 007 can be generated on the display screen. An adjustment module comprises the camera 9, the PLC 8 and the display screen 7.

The filter assembly 2 comprises a first mounting plate 21, a first upper slide bar 22 and a first lower slide bar 23 mounted on the first mounting plate 21, and a first filter 24 and a second filter 25 slidably connected to the first upper slide bar 22 and the first lower slide bar 23; on the same side of the first filter 24 and the second filter 25 are provided with guide grooves 26. There are two first upper slide bars 22 and two first lower slide bars 23 respectively arranged in parallel, and the first upper slide bars 22 are located above the first lower slide bars 23; the filter assembly 2 further comprises a first drive motor 27 mounted on the first mounting plate 21, a first variable gear 28 fixedly sleeved on a rotating shaft of the first drive motor 27, a second gear 29 rotatably connected to the first mounting plate 21 and in transmission connection with the first variable gear 28, a first guide rod 20 and a second guide rod 210 fixed on the end surface of the second gear 29 a first travel sensor 211 for detecting a movement position of the filters by counting the number of turns of the second gear 29, and an illuminometer assembly 212, wherein the first guide rod 20 is inserted in the guide grooves 26 on the first filter 24, and the second guide rod 210 is inserted in the guide grooves 26 on the second filter 25, and the second gear 29 is configured to rotate to drive the first filter 24 and the second filter 25 to slide in opposite directions respectively on the first upper slide bars 22 and the first lower slide bars 23.

The collimating sheet assembly 1 comprises a second mounting plate 11, an upper support 12 and a lower support 13 mounted on the second mounting plate 11, an upper guide shaft 14 and a lower guide shaft 15 respectively mounted on the upper support 12 and the lower support 13, an upper shielding sheet 16 and a lower shielding sheet 17 slidably connected to the upper guide shaft 14 and the lower guide shaft 15, an upper driving screw mechanism and a lower driving screw mechanism for respectively driving the upper shielding sheet 16 to slide on the upper guide shaft 14 and driving the lower shielding sheet 17 to slide on the lower guide shaft 15, and an upper travel sensor 18 and a lower travel sensor 19 for respectively detecting a moving distance of the upper shielding sheet 16 and a moving distance of the lower shielding sheet 17, wherein the sliding directions of the upper shielding sheet 16 and the lower shielding sheet 17 are perpendicular to each other. The upper driving screw mechanism comprises an upper second motor 10, an upper second gear set 111 in transmission connection with the upper second motor 10, an upper screw 112 arranged in parallel with the upper guide shaft 14, and an upper mounting frame 113 fixedly connected with a transmission nut of the upper screw 112, wherein the upper screw 112 is in transmission connection with the upper second gear set 111, and the upper shielding sheet 16 is mounted on the upper mounting frame 113, and there are respectively two upper mounting frames 113 and two upper shielding sheets 16. The lower driving screw mechanism comprises a lower second motor 110, a lower second gear set 114 in transmission connection with the lower second motor 110, a lower screw 115 arranged in parallel with the lower guide shaft 15, and a lower mounting frame 116 fixedly connected with a transmission nut of the lower screw 115, wherein the lower screw 115 is in transmission connection with the lower second gear set 114, and the lower shielding sheet 17 is mounted on the lower mounting frame 116, and there are respectively two lower mounting frames 116 and two lower shielding sheets 17.

The principle of imaging and projection area 007 will be described in detail with reference to FIG. 4:

1. The relevant variables and constants are as follows:

Co_y(collimator_offset_y): an offset distance from a collimator opening to a focus of X-ray tube in the vertical direction (unit; mm)

Co_x(camera_offset_x): an offset distance from a camera to a focus of tube in the horizontal direction (unit: mm)

Dw(detector_width): a width of an imaging area of an X-ray detector (unit:

Dh(detector_height): a height of an imaging area of an X-ray detector (unit: mm)
(D_x, D_y): a center coordinate of the X-ray detector displayed in a screen (unit: pixel)
CID(camera to image-receptor distance): a distance from a camera to an image-receiver (unit: mm)
FW(field_width): a width that a camera can cover when the CID is determined (unit: mm)
w(width pixel): a width of an image in pixels (unit: pixel)
f: a intrinsic parameter of a camera 2. the intrinsic parameter of a camera As shown in FIG. 3, the width of an image in pixels is correspondingly obtained according to a pinhole model:

$$w = f \frac{FW}{CID}$$

wherein, the camera parameter f is provided by the camera manufacturer.

3. Correspondence among adjustment of screen pixels, a displacement of a receiver, and a displacement of a collimating opening 3) An interactive interface adjusts the pixels by $\Delta w$ (pixel), and the imaging area of an X-ray detector is shifted by $\Delta FW$ (mm). From the previous formula:

$$FW = \frac{CID}{f} * w$$

A discretization form could be available:

$$\Delta FW = \frac{CID}{f} * \Delta w$$

in the formula, CID is a distance from the camera to the imaging area of the X-ray detector, which can be measured in real time: f is a known value; and when the width of the interactive interface is shifted by $\Delta w$ (pixel), the imaging area of the X-ray detector is shifted by $\Delta FW$ (mm).

4) The interactive interface adjusts the pixels by $\Delta w$ (pixel), and the collimator opening driving motor is shifted by $\Delta c$ (mm). From the similar triangle formulas:

$$\frac{\Delta c}{\Delta FW} = \frac{Co\_y}{CID + Co\_y}$$

Following formula could be derived:

$$\Delta c = \frac{Co\_y}{CID + Co\_y} \Delta FW$$

The $\Delta FW$ is brought in to obtain the following formula:

$$\Delta c = \frac{CID}{f} * \frac{Co\_y}{CID + Co\_y} \Delta w$$

in the formula; CID is the distance from the camera to the imaging area of the X-ray detector, which can be measured in real time, the rest are known values, and when the width of the interactive interface is shifted by $\Delta w$ (pixel), the collimator opening is shifted by $\Delta c$ (mm).

Correspondingly, the number of pulses that the system needs to send to the stepper motor driver can be obtained. As a single pulse displacement of the stepper motor is known as:

$$\frac{n\theta}{360°} * k * L,$$

where $\theta$ is a step angle, n is a subdivision number of the driver, k is a gear ratio, and L is a lead of screw. Therefore, when is required to shift the collimator opening by $\Delta c$, the number of pulses N_pulse that the system needs to send to the driver is:

$$N\_pulse = \frac{\Delta c}{\frac{n\theta}{360°} * k * L}$$

The adjustment of parameter of the detector refers to the exposure system disclosed in the patent with patent publication number CN106954329B, which is hereby incorporated by reference herein in its entirety.

As shown in FIG. 1, the maximum exposure acceptance range of the detector is the effective imaging area 006, and an imaging method based on the above system, comprises the following steps:

a. A subject 009 to be X-ray imaged is configured to enter the imaging system to ensure that the subject 009 is within the effective imaging area 006;

b. The camera 9 is configured to display the subject 009 and the projection area 007 on the display screen 7 in real-time;

c. The projection area 007 has a corresponding projection image frame on the display screen 7, and the user selects the projection image frame on the display screen 7 using a mouse of the host computer 005 and drags it to a desired observation position; the PLC 8 converts the displacement of each side of the projection image frame on the display screen 7 into the respectively required adjustment displacement of the collimating sheet assembly 1, and then each side of the projection image frame is respectively adjusted to the required coverage position by the collimating sheet assembly, to form the projection area 007;

d. The desired filter serial number is selected on the display screen 7, and the PLC controls the action of the filter assembly 2 to adjust to a desired filter;

e. The position information of the area of interest is transmitted to the flat-panel detector 004, and the flat-panel detector 004 calculates the automatic exposure control parameters (DAEC parameters) according to the information of the area and the demand of the diagnostic part and/or position;

f. The system starts to expose after the actions of the collimating sheet assembly 1 and the filter assembly 2 have been completed;

g. According to the automatic exposure control parameters, the detector automatically informs the high-voltage generator to stop exposure, and an X-ray image is obtained.

Although the present invention has been disclosed in the form of preferred embodiments and variations thereon, it will be understood that numerous additional modifications and variations could be made thereto without departing from the scope of the invention.

For the sake of clarity, it is to be understood that the use of 'a' or 'an' throughout this application does not exclude a plurality, and 'comprising' does not exclude other steps or elements.

The invention claimed is:

1. An X-ray imaging system, comprising an X-ray source, a high-voltage generator, a collimator, a digital flat-panel detector, and a host computer, wherein the host computer is configured to implement a signal transmission and processing among the X-ray source, the high-voltage generator, the collimator and the digital flat-panel detector, wherein the collimator comprises a collimating sheet assembly that makes light form a projection area on a subject; the digital flat-panel detector is configured to have a digital automatic exposure control (DAEC) function and configured to be able to generate a DAEC parameter which comprises an actual DAEC response area and a target gray value, wherein the system further comprises a programmable logic controller (PLC) and a camera for capturing an image of the subject, the PLC is configured to display the image captured by the camera on a display screen, and generate a coordinate system and a projection image frame corresponding to the projection area on the display screen, wherein a pixel of a captured image and a coordinate point of the coordinate system form a one-to-one correspondence, and the PLC is configured to automatically determine the projection area and the actual DAEC response area to a desired position according to the captured image and a demand of a diagnostic part and/or position, the projection area is configured to be adjusted according to the demand of the diagnostic part and/or position or an adjustment of the projection image frame, and the projection area is adjusted by the collimating sheet assembly; the actual DAEC response area is configured to be adjusted according to the demand of the diagnostic part and/or position, and the actual DAEC response area is adjusted by the digital flat-panel detector; the projection area is configured to cover the actual DAEC response area, the display screen is connected to the PLC; the PLC is arranged in the collimator; the projection image frame and a frame of the response area would or would not be displayed on the display screen.

2. An X-ray imaging system, comprising an X-ray source, a high-voltage generator, a collimator, a digital flat-panel detector, and a host computer, wherein the host computer is configured to implement a signal transmission and processing among the X-ray source, the high-voltage generator, the collimator and the digital flat-panel detector, wherein the collimator comprises a collimating sheet assembly that makes light form a projection area on a subject, the digital flat-panel detector is configured to have a digital automatic exposure control (DAEC) function and be able to generate a DAEC parameter which comprises an actual DAEC response area and a target gray value, wherein the system further comprises a camera for capturing an image of the subject, and an adjustment module for automatically adjusting the projection area and the actual DAEC response area to a desired position according to the image captured by the camera and a demand of a diagnostic part and/or position.

3. The X-ray imaging system according to claim 2, wherein the projection area is configured to cover the actual DAEC response area.

4. The X-ray imaging system according to claim 2, wherein the adjustment module comprises a programmable logic controller (PLC), the PLC is configured to display the image captured by the camera on a display screen, and generate a coordinate system and a projection image frame corresponding to the projection area on the display screen, wherein a pixel of a captured image and a coordinate point of the coordinate system form a one-to-one correspondence;

as the projection image frame corresponding to the projection area is generated on the display screen, the projection area is configured to be adjusted according to the demand of the diagnostic part and/or position or an adjustment of the projection image frame, and the actual DAEC response area is configured to be adjusted according to a demand of an adjustment of the diagnostic part and/or position.

5. The X-ray imaging system according to claim 4, wherein the display screen is configured to be a display screen connected to the PLC or to the host computer.

6. The X-ray imaging system according to claim 4, wherein the PLC is a part of the host computer or is arranged in the collimator, and the projection image frame and a frame of the response area would or would not be displayed on the display screen.

7. The X-ray imaging system according to claim 2, wherein the adjustment module comprises an intelligent recognition module for recognizing an examined part of the subject presented by the camera, the intelligent recognition module is connected with the collimator and the digital flat-panel detector;

the intelligent recognition module is configured to adjust the projection area and the actual DAEC response area according to a demand of an input diagnostic part and/or position as the intelligent recognition module has recognized the examined part of the subject, a positional relationship between the examined part and a current projection area, and a positional relation between the examined part and a current actual DAEC response area.

8. The X-ray imaging system according to claim 2, wherein a maximum exposure acceptance range of a detector is configured to be an effective imaging area, the system configured to perform operations comprising the following steps:

a1. causing a subject to be X-ray imaged to enter the imaging system to ensure that the subject is within the effective imaging area;

b1. photographing the subject by the camera, displaying an image captured by the camera on a display screen, and generating a coordinate system and a projection image frame corresponding to a projection area on the display screen by an adjustment module;

c1. adjusting the projection area and an actual DAEC response area to a desired position by the adjustment module according to a demand of a diagnostic part and/or position;

d1. determining a target gray value according to the demand of the diagnostic part and/or position;

e1. automatically informing a high-voltage generator to stop exposure according to a DAEC parameter during the X-ray photographing process, and obtaining an X-ray image by the detector;

wherein step c1 and step d1 are in no particular order.

9. The X-ray imaging system according to claim 4, wherein a maximum exposure acceptance range of a digital flat-panel detector is configured to be an effective imaging area, the system configured to perform operations comprising the following steps:
- a2. causing a subject to be X-ray imaged to enter the imaging system to ensure that the subject is within the effective imaging area;
- b2. photographing the subject by the camera, displaying an image captured by the camera on a display screen, and generating a coordinate system and a projection image frame corresponding to a projection area on the display screen by an adjustment module;
- c2. touching the projection image frame on the display screen and dragging it to a desired observation position; or circling or pointing out an area of interest on the display screen to form a new image frame,
- a PLC is configured to convert a displacement of each side of the image frame on the display screen into the respectively required adjustment displacement of a collimating sheet assembly; a projection area is configured to be formed as the collimating sheet assembly is respectively adjusted to a required coverage position;
- d2. transmitting a position information of the area of interest to the flat-panel detector, and adjusting an automatic exposure control parameter according to the position information of the area and a demand of a diagnostic part and/or position by the flat-panel detector;
- e2. starting to expose as an action of the collimating sheet assembly is completed and the automatic exposure control parameter is determined;
- f2. automatically informing a high-voltage generator to stop exposure according to the automatic exposure control parameter, and obtaining an X-ray image by the detector.

10. The X-ray imaging system according to claim 7, the system further comprising an intelligent recognition module for recognizing an examined part of a subject presented on a display screen by a camera, and a maximum exposure acceptance range of a digital flat-panel detector is configured to be an effective imaging area, wherein the digital flat-panel detector has a function for automatically generating a DAEC parameter, the system configured to perform operations comprising the following steps:
- a3. causing a subject to be X-ray imaged to enter the imaging system to ensure that the subject is within the effective imaging area;
- b3. photographing the subject and the detector by the camera, and recognizing the examined part of the subject, a positional relationship between the examined part and a current projection area, and a positional relation between the examined part and a current actual DAEC response area by the intelligent recognition module after receiving and processing a captured image;
- c3. adjusting the projection area and the actual DAEC response area by the intelligent recognition module according to a demand of a diagnostic part and/or position;
- d3. adjusting an automatic exposure control parameter through the flat-panel detector according to the demand of the diagnostic part and/or position;
- e3. starting to expose as an action of a collimating sheet assembly is completed and the automatic exposure control parameter is determined;
- f3. automatically informing a high-voltage generator to stop exposure according to the automatic exposure control parameter, and obtaining an X-ray image by the detector.

* * * * *